United States Patent [19]
Fedorov et al.

[11] Patent Number: 5,993,796
[45] Date of Patent: Nov. 30, 1999

[54] BIOCOMPATIBLE POLYMERIC MATERIALS, METHODS OF PREPARING SUCH MATERIALS AND USES THEREOF

[75] Inventors: Svyatoslav Nikolayevich Fedorov; Sergei Nikolayevich Bagrov; Irina Aleksandrovna Maklakova; Sergei Viktorovich Novikov; Galina Dmitriyevna Shelukhina, all of Moscow, Russian Federation

[73] Assignee: Staar Surgical AG, Nidau, Switzerland

[21] Appl. No.: 08/751,706

[22] Filed: Nov. 18, 1996

[51] Int. Cl.[6] .......................... A61K 47/42; C08L 89/00; C08J 3/24; C08F 283/04
[52] U.S. Cl. ................. 424/78.17; 514/773; 525/54.1; 525/426; 264/1.36; 264/299; 523/106; 522/87
[58] Field of Search ................................ 424/486, 484, 424/78.17, 78.37; 514/773; 525/54.1, 426; 264/1.36, 299; 530/356; 522/87; 529/937; 523/106

[56] References Cited

U.S. PATENT DOCUMENTS

| | | | |
|---|---|---|---|
| Re. 33,997 | 7/1992 | Kuzma et al. | 523/106 |
| 4,042,457 | 8/1977 | Kuettner et al. | 195/1.8 |
| 4,064,008 | 12/1977 | Petersen et al. | 195/6 |
| 4,220,724 | 9/1980 | Berg et al. | 435/273 |
| 4,563,490 | 1/1986 | Stol et al. . | |
| 4,876,332 | 10/1989 | Tsilibary et al. | 530/326 |
| 4,894,441 | 1/1990 | Menicagli | 530/356 |
| 5,103,840 | 4/1992 | Kavoussi | 128/899 |
| 5,114,627 | 5/1992 | Civgrchia . | |
| 5,210,182 | 5/1993 | Nasrallah et al. | 530/355 |
| 5,286,829 | 2/1994 | Fedorov et al. . | |
| 5,424,408 | 6/1995 | Reeders et al. | 536/23 |
| 5,476,515 | 12/1995 | Kelman et al. | 623/6 |
| 5,632,773 | 5/1997 | Graham et al. . | |
| 5,635,482 | 6/1997 | Bhatnagar . | |
| 5,654,349 | 8/1997 | Feingold et al. . | |

*Primary Examiner*—Edward J. Webman
*Attorney, Agent, or Firm*—Klima & Pezzlo, P.C.

[57] ABSTRACT

The present invention is directed to a biocompatible polymeric material and methods of making prepared by forming a mixture of collagen, a water-soluble ethylenically unsaturated compound and a cross-linking agent at a temperature of 30° C. to 42° C.; adjusting the pH of the mixture to 3.2 to 5.0; and polymerizing the mixture. The resulting material is rinsed in a physiologic solution at a temperature of 25° C. to 80° C. The resulting polymeric material has a modules of elasticity in the range of 10 to $27 \times 10^5$ $N/m^2$. Mechanical strength of the polymeric material is 20 to 100 times greater than polymeric material prepared by known methods. The material is optically transparent and is characterized by 95% or more light transmission in the visible spectrum and by resolution of 200 lines per mm for a +20D intraocular lens. The material is characterized by low protein absorption of about $0.1 \times 10^{-3}$ $\mu g/mg$ and the material is resistant to proteolytic enzymes including pepsin, trypsin, chymotrypsin, and collagenase. The present invention is further directed to intraocular lenses and contact lenses produced from the present material, and the use of such lenses in patients having impaired vision to correct or improve such impaired vision.

15 Claims, No Drawings

BIOCOMPATIBLE POLYMERIC MATERIALS, METHODS OF PREPARING SUCH MATERIALS AND USES THEREOF

FIELD OF THE INVENTION

The invention relates to biocompatible polymeric materials that can be used for intraocular and contact lenses, and methods for producing such materials.

BACKGROUND OF THE INVENTION

Known methods for extracting collagen include extracting collagen from calf hide by grinding the hide, rinsing the ground hide with a solution of sodium bicarbonate and water, centrifuging and dissolving the recovered solid in water at a pH of 3.0. The resulting collagen solution is then treated with pepsin for 5 to 10 days to remove the telopeptides (non-helical end portions) from the tropocollagen to produce atelocollagen ("soluble" collagen lacking telopeptide). The atelocollagen solution is then filtered through a 0.65 μ MILLIPORE filter, is re-precipitated by raising the solution pH and the precipitate is then separated by centrifugation and then lyophilized to dry. The dried collagen is then dissolved in distilled water by acidification with 0.1 M HCl to a pH of 3.0. An ethylenically unsaturated compound and a cross linking agent are added thereto and the resulting mixture is placed in disposable plastic syringes, degassed, centrifuged to remove bubbles and then poured into contact lens molds under a nitrogen atmosphere. The mixture is then exposed to gamma-irradiation. The resulting lenses are neutralized in BOIL 'N SOAK™, Burton, Parsons & Co., Inc., according to U.S. Pat. No.: Re. 33,997 to Kuzma et al.

Kuzma's method is problematic in that it results in weak atelocollagen-based hydrogels that do not allow the production of permanent intraocular lenses that can be implanted into the eye. The present invention provides a strong, collagen based hydrogel suitable for producing permanent intraocular lenses for implantation into the eye of a patient.

SUMMARY OF THE INVENTION

The present invention provides a method of preparing a biocompatible polymeric material and the material produced thereby. The method includes forming a mixture of: collagen, one or more water-soluble ethylenically unsaturated compounds, and a cross linking agent, at a temperature of from 30° C. to 42° C., preferably from 35° C. to 40° C., and adjusting pH of the mixture to from 3.2 to 5.0, preferably from 3.5 to 4.2. The mixture is then polymerized for example using radiation to produce the present biocompatible polymeric material.

An object of the present invention is to synthesize strong, optically transparent, biocompatible materials suitable for use as ophthalmological implants and as contact lenses.

Another object is to provide a biocompatible material that is elastic, characterized by low protein absorption and is resistant to proteolytic enzymes including for example pepsin, trypsin, chymotrypsin, and collagenase.

A further object of the present invention is a contact lens or an intraocular lens characterized by having a modulus of elasticity $10 \times 10^5$ N/m$^2$ or greater and light transmission of 95% or greater.

DETAILED DESCRIPTION OF THE INVENTION

A. Methods of Producing the Present Material:

An acidic solution of fibrillar collagen or atelocollagen or a mixture thereof is suitable for use in the present invention. The collagen is preferably extracted from farm animal ocular sclera. The collagen may be extracted from raw material by any known method. For example, the internal membranes, remnants of the conjunctiva and the muscles are carefully removed from the ocular sclera of the eyes of farm animals and then the stroma is excised. Pigmented portions of the stroma are cut away and discarded. The remainder of the stroma is cut into small pieces and thoroughly rinsed with distilled water. The pieces are then put into a flask. A 10% solution of an alkali metal hydroxide saturated with a sulfate of the same metal is added to the flask for 48 hours at a temperature of 20° C. to provide a concentration of 3000 milliliters of solution per 60 grams of tissue. The solution is drained and the tissue is then rinsed with distilled water until all of the sulfate ion is removed. The tissue is neutralized to a pH of 6.0 by stirring in sequential 2% boric acid solutions. The tissue is then rinsed with distilled water to remove all borate ions and a 0.5 M solution of acetic acid is added to provide a final collagen concentration of 0.5 to 20% in the solution. The solution is stirred and left for 1 to 2 days at a temperature of 4–10° C. The solution is then homogenized and filtered through a glass filter. The resultant fibrillar collagen solution is ready for use. If desired, the solution can also be treated with an enzyme (trypsin, pepsin, etc., but not collagenase) to produce atelocollagen.

The water-soluble, ethylenically unsaturated compound is preferably 2-hydroxy ethyl methacrylate, acrylamide, N-vinyl pyrrolidone or mixtures thereof, or functional equivalents thereof. Suitable functional equivalents can be readily selected by one of ordinary skill in the art to which the present invention pertains.

The cross-linking agent is preferably an ethylene glycol diacrylate and/or an ethylene glycol dimethacrylate based compound having 1 to 13 repeating ethylene glycol units.

The collagen concentration in the mixture can vary from 0.001% to 5.0%, the concentration of the water-soluble, ethylenically unsaturated compound can vary from 55% to 99% and the concentration of the cross-linking agent can vary from 0.1 to 1.0%.

The 30° C. to 42° C. temperature range for forming the mixture in accordance with the invention is important because below 30° C., the collagen molecules are not completely dehydrated while temperatures above 42° C. result in denatured collagen. If the collagen is not completely dehydrated, a coarse dispersion results in the mixture which adversely affects the optical characteristics of the resulting polymeric material. If the collagen is denatured, the physical and mechanical characteristics of the polymeric material are adversely affected.

The pH of the mixture must be adjusted to from 3.2 to 5.0 because a pH above 5.0 causes the collagen molecules to aggregate. This aggregation adversely affects optical characteristics of the resulting polymer. A pH below 3.2 alters the reactivity of the ethylenically unsaturated compound to adversely affect mechanical properties of the final polymer.

The pH can be adjusted using for example, acetic or hydrochloric acid and stirring. The adjusted mixture is then degassed, saturated with an inert gas, degassed again, poured into molds of required configuration, and polymerized using gamma irradiation in doses of from 0.3 to 2.0 Mrads.

The end product (lens) is then cleaned by rinsing with a physiologic solution at a temperature of from 25° C. to 80°

C. The rinsing removes low molecular weight polymerization products. Temperatures lower than 25° C. slow down the diffusion rate of the low molecular weight products, thus making the polymerization products difficult to remove. At temperatures above 80° C., the polymeric material partially breaks down.

B. Characterization of the Produced Maternal:

The method of the present invention results in a biocompatible polymeric material that is very strong and elastic. The modulus of elasticity of the present material is greater than $10 \times 10^5$ N/m$^2$, preferably in the range of from 10 to $27 \times 10^5$ N/M$^2$, more preferably 15 to $27 \times 10^5$ N/m$^2$. Mechanical strength is 20 to 100 times greater than prior art polymeric materials. The present polymeric material is optically transparent and is characterized by 95% or greater light transmission in the visible spectrum, preferably 96% or greater, more preferably 98% or greater, and by a resolution of 200 lines per mm for a +20D intraocular lens. The present material is characterized by low protein absorption of about $0.1 \times 10^{-3}$ µg/mg or less and the material is resistant to proteolytic enzymes including but not limited to pepsin, trypsin, chymotrypsin, and collagenase.

C. Biocompatibility:

The present polymeric material was synthesized by the present method and was tested for biocompatibility on the basis of adhesion of cultured fibroblastic (a culture of keratocytes) and macrophage cells (peritoneal macrophage). A macrophage cell suspension was added to culture medium with 20 mm×20 mm test pieces of the present polymeric material. The corneal fibroblasts spread out well and adhered to the present polymeric material. Inflammatory cells did not adhere to the present polymeric material.

In a series of experiments, intraocular lenses made of the present polymeric material were placed in rabbits' eyes. Biocompatability of the material was evaluated against clinical and morphological standards. At three days post-implant, mild corneal edema was observed in the vicinity of the incision. No precipitates were observed on the surface of the lenses. Thereafter, no changes in the ocular membranes were observed. A morphological examination revealed abnormally shaped endothelial cells in the implant area after the first week. Mild ectasia of the iris was observed two weeks after the operation. No other changes in eye tissue were thereafter observed.

Clinical tests following the above implantation were then conducted. The eye tissues exhibited no adverse reaction to the present polymeric material from the first day post-implant. Further, no precipitates were observed on the surfaces of the lenses. These observations indicate that the present polymeric material is highly biocompatible. The present material is characterized by its strength and elasticity which characteristics allow for atraumatic and quick implantation of an intraocular lens. The present lenses have good optical characteristics as evidenced in good eyesight and visual acuity of the patients.

EXAMPLES

The following examples are intended to illustrate the invention without limiting its scope.

Example I 79 grams of 2-hydroxy ethyl methacrylate was gradually added at 35° C. to 20 grams of a 5% fibrillar collagen solution obtained from farm animal eye sclera. The mixture was stirred while the pH was maintained at 4.0. One gram of 3-ethylene glycol diacrylate was then added. The mixture was then completely blended, thereafter degassed, saturated with argon, degassed again and finally poured into intraocular lens molds. Polymerization was carried out by irradiation with 1.8 Mrads of gamma radiation. The intraocular lenses were then removed from the molds and rinsed in a physiologic solution at a temperature of 70° C. to remove low molecular weight polymerization products.

The resulting intraocular lens had a modules of elasticity of $20 \times 10^5$ N/m$^2$ and an optical transparency of 97%. The lens was then implanted in a rabbit's eye. A zero-degree reaction was observed, indicating good biocompatibility.

Example II

Twenty-five grams of a 20% atelocollagen solution was heated to 30° C. 5.2 grams of acrylamide and 70.0 grams of 2-hydroxy ethyl methacrylate were slowly added to the atelocollagen solution with the temperature maintained at 30° C. and the pH maintained at 3.5 with acetic acid. 0.8 grams of 13-ethylene glycol methacrylate was then added with the foregoing conditions maintained. The mixture was degassed, saturated with nitrogen, degassed again, and carefully poured into intraocular lens molds. The molds were cooled to 4° C. and were polymerized by irradiation with 1.0 Mrad of gamma radiation. The resulting intraocular lenses were removed from the molds and rinsed in a physiologic solution at a temperature of 40° C.

The resulting intraocular lenses had a modules of elasticity of $18 \times 10^5$ N/m$^2$ and an optical transparency of 96%.

Example III

Five grams of 5% atelocollagen were mixed with 5 grams of 5% fibrillar collagen and heated to 40° C. 89 grams of vinyl pyrrolidone were then added to the mixture while pH was maintained at 4.2. 1.0 gram of 3-ethylene glycol dimethacrylate was then added to the mixture. The mixture was then degassed, saturated with argon, degassed again and poured into contact lens molds. The molds were irradiated with a dose of 2.0 Mrads of gamma radiation at a temperature of 4° C. The resulting intraocular lenses were removed from the molds and rinsed in a physiologic solution at a temperature of 45° C.

The resulting contact lens had a transparency of 98% and a modules of elasticity of $15 \times 10^5$ N/m$^2$.

Thereafter, the contact lens was placed on a patient's cornea. On the second day post-placement, no significant edema of the cornea was observed (edema was 0.1%) indicating a high level of biocompatibility.

The above examples illustrate that the present material and method produces a biocompatible material that is strong, optically transparent and resistant to enzymes, The present material can be used to produce ophthalmological surgical implants such as intraocular lenses and to produce contact lenses.

Other modifications of the present invention will occur to those skilled in the art subsequent to a review of the present application. These modifications and equivalents thereof are intended to be included within the scope of the invention.

What is claimed:

1. A method of preparing a biocompatible polymeric material, comprising the steps of:
   mixing together collagen, a water-soluble ethylenically unsaturated compound, and a cross-linking agent to form a mixture, at a temperature of from 30° C. to 42°;
   adjusting a pH of said mixture from 3.2 to 5.0; and
   polymerizing said mixture to produce the biocompatible polymeric material.

2. The method of claim 1, further comprising:
rinsing produced biocompatible polymeric material in a physiologic solution at a temperature of from 25° C. to 80° C.

3. The method of claim 2, wherein said rinsing is carried out for a time effective to remove any low-molecular weight post-polymerization products present on the biocompatible polymeric material.

4. The method of claim 1, further comprising:
prior to said step of forming, extracting said collagen from animal eye sclera.

5. The method of any one of claims 1 or 2, wherein said collagen comprises one or more members selected from the group consisting of: fibrillar collagen and atelocollagen.

6. The method of claim 1, wherein said water-soluble ethylenically unsaturated compound comprises one or more members selected from the group consisting of:
2-hydroxy ethyl methacrylate, acrylamide and N-vinyl pyrrolidone.

7. The method of claim 1, wherein said cross-linking agent comprises one or more members selected from the group consisting of:
an ethylene glycol diacrylate having 1 to 13 repeating ethylene glycol units and an ethylene glycol dimethacrylate based compound having 1 to 13 repeating ethylene glycol units.

8. The method of claim 1, wherein said mixture comprises 0.001% to 5.0% collagen, 55% to 99% water soluble ethylenically unsaturated compound and 0.1 to 1.0% cross-linking agent.

9. The method of claim 1, further comprising:
after said step of adjusting the pH and prior to said step of polymerizing, pouring said mixture into an intraocular or a contact lens shaped mold.

10. The method of claim 1, wherein said polymerizing step comprises irradiating said mixture to produce a biocompatible polymeric material in the shape of an intraocular lens or contact lens.

11. The method of claim 10, further comprising:
positioning said contact lens on a surface of an eye of a patient.

12. The method of claim 9, wherein said polymerizing step comprises irradiating said mixture to produce a biocompatible polymeric material in the shape of an intraocular lens or contact lens.

13. The method of claim 10, further comprising:
implanting said intraocular lens into an eye of a patient.

14. The method of claim 10, further comprising:
positioning said contact lens on a surface of an eye of a patient.

15. A method of preparing a biocompatible polymeric material, comprising the steps of:
mixing together collagen, a water-soluble ethylenically unsaturated compound, and a cross-linking agent to form a mixture, at a temperature of from 30° C. to 42°;
adjusting a pH of said mixture from 3.2 to 5.0; and
polymerizing said mixture using gamma radiation in doses from 0.3 to 2.0 Mrads.

* * * * *